(12) United States Patent  
Carpenter

(10) Patent No.: US 7,172,730 B2  
(45) Date of Patent: Feb. 6, 2007

(54) THERMAL SENSOR

(75) Inventor: Steven E. Carpenter, Philomath, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 516 days.

(21) Appl. No.: 10/315,461

(22) Filed: Dec. 9, 2002

(65) Prior Publication Data

US 2004/0110300 A1    Jun. 10, 2004

(51) Int. Cl.
- B32B 5/02   (2006.01)
- B32B 27/04  (2006.01)
- B32B 27/12  (2006.01)
- G01N 30/96  (2006.01)
- G01N 1/00   (2006.01)

(52) U.S. Cl. .................... 422/88; 422/50; 422/52; 422/54; 422/56; 422/58; 422/68.1; 422/69; 422/80; 422/81; 422/83; 422/89; 422/100; 422/101; 422/103; 422/104; 436/43; 436/174; 436/178; 436/181; 73/1.01; 73/1.02; 73/23.2; 73/53.01

(58) Field of Classification Search .................. 422/50, 422/52, 54, 56, 58, 68.1, 69, 80, 81, 83, 88, 422/89, 100, 101, 103, 104; 436/43, 174, 436/178, 181; 73/1.01, 1.02, 23.2, 53.01
See application file for complete search history.

(56) References Cited

U.S. PATENT DOCUMENTS

| | | | | |
|---|---|---|---|---|
| 3,867,098 A | * | 2/1975 | Gorkovenko et al. | 422/88 |
| 4,711,765 A | * | 12/1987 | Cates et al. | 422/89 |
| 4,805,441 A | * | 2/1989 | Sides et al. | 73/23.25 |
| 4,912,051 A | * | 3/1990 | Zaromb | 436/178 |
| 5,232,667 A | * | 8/1993 | Hieb et al. | 422/82.04 |
| 5,469,369 A | * | 11/1995 | Rose-Pehrsson et al. | 702/27 |
| 5,661,036 A | * | 8/1997 | Benner et al. | 436/123 |
| 5,854,431 A | * | 12/1998 | Linker et al. | 73/863.23 |
| 5,888,830 A | | 3/1999 | Mahan et al. | |
| 6,034,775 A | | 3/2000 | McFarland et al. | |
| 6,171,378 B1 | * | 1/2001 | Manginell et al. | 96/143 |
| 6,410,332 B1 | | 6/2002 | Desrosiers et al. | |
| 6,604,406 B1 | * | 8/2003 | Linker et al. | 73/28.02 |
| 6,656,738 B1 | * | 12/2003 | Vogel et al. | 436/161 |

* cited by examiner

Primary Examiner—Brian Sines

(57) ABSTRACT

A thermal sensor has a substrate defining a reaction chamber. The reaction chamber has an inlet for conducting sample into the reaction chamber, a reaction surface and an orifice adjacent the reaction surface defining an outlet from the reaction chamber. The reaction surface is coated with a sorbant for binding agents in the sample. A heat transducer in the substrate and in proximity to the reaction surface is configured for heating the reaction surface.

23 Claims, 3 Drawing Sheets

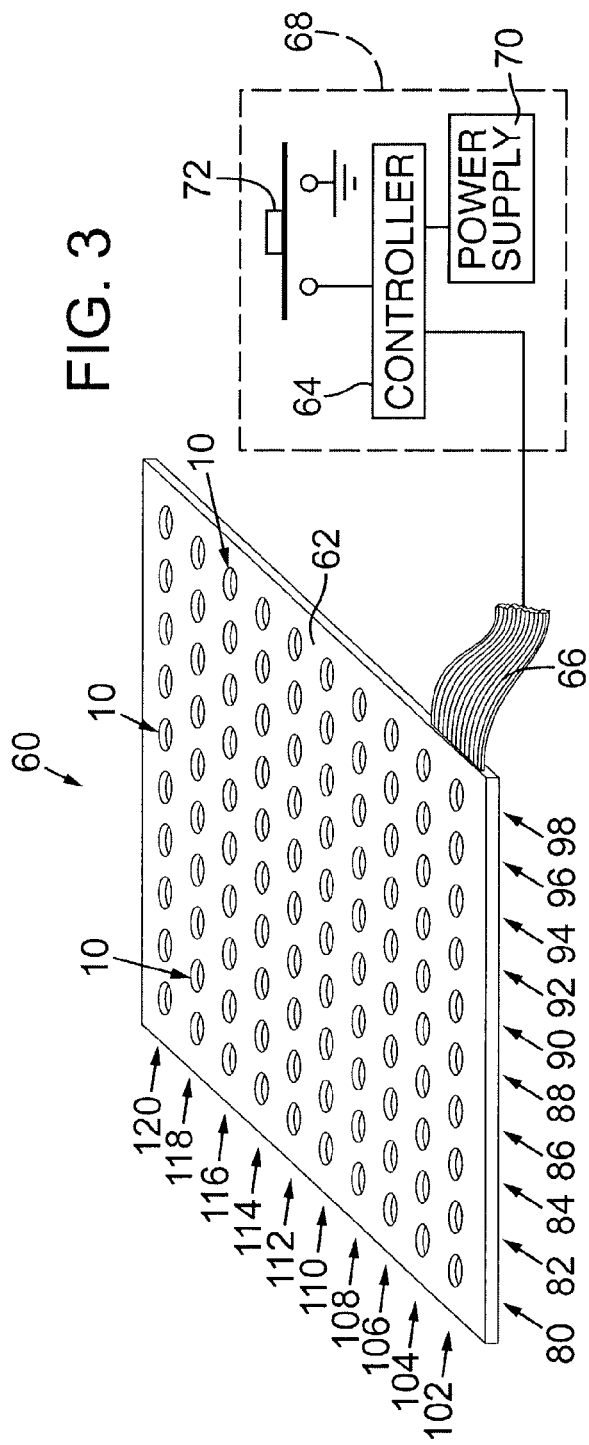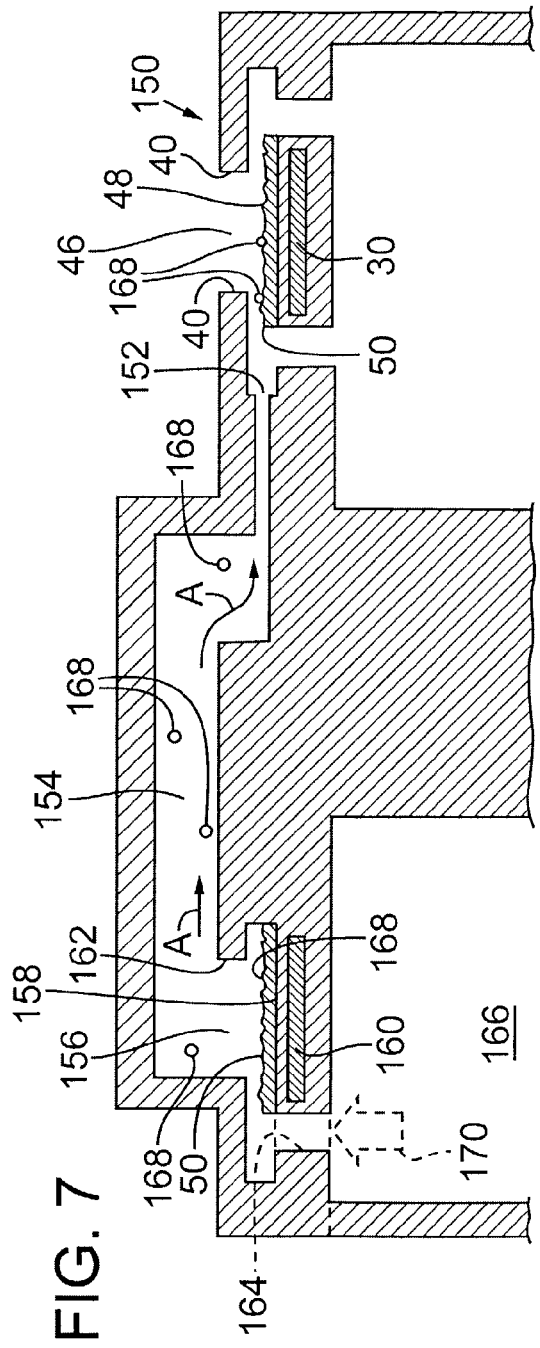

THERMAL SENSOR

TECHNICAL FIELD

This invention relates to apparatus for analyzing environmental agents such as organic and inorganic compounds, using sorbant-coated reaction surfaces to attract and bind the agents. The reaction surfaces are heated to volatilize the agents so that they may be detected by and characterized with analytical instruments.

BACKGROUND OF THE INVENTION

The ability to detect the presence of various chemical compounds in a given environment, and to characterize those compounds on a rapid turnaround basis is of great practical importance. To cite just a few examples, industrial settings often rely upon ongoing monitoring and analysis of various chemicals in effluent, such as a waste streams, to ensure that waste discharges are in compliance with regulations. Likewise, military operations often rely upon the ability to rapidly detect and characterize various molecules and other agents in specific environments. The need for apparatus designed for use in the field, where traditional laboratory instruments are ill suited to be used, and for use in harsh environments is particularly acute.

Passive sample collection is one technique that is used to monitor chemicals in the environment. Using this methodology, sample collection devices, often using activated charcoal, are coated with sorbants such as expanded polymers. The devices are exposed to the environment so that chemicals in the environment bind to the sorbant material. The devices are then sent to a laboratory, typically at a remote location, where the bound chemicals are desorbed from the charcoal and analyzed.

While there are numerous ongoing advances being made in analytical chemistry that are providing promising techniques for detecting and characterizing various compounds found in an environment, it can be appreciated that a need exists for apparatus capable of rapidly detecting the presence of chemicals in a sample. There is an especially significant and ongoing need for apparatus and methods that allow for rapid detection of the presence of chemicals in an environment, and that also facilitate chemical analysis compounds of interest.

Apparatus and methods addressing this need are described in detail below. Advantages and features of the illustrated invention will become clear upon review of the following specification and drawings.

SUMMARY

The illustrated embodiment comprises a substrate defining a reaction chamber having an inlet for conducting fluid into the reaction chamber, a reaction surface and an orifice adjacent the reaction surface defining an outlet from the reaction chamber. The reaction surface has a sorbant deposited thereon and a heat transducer in the substrate heats the reaction surface.

BRIEF DESCRIPTION OF THE DRAWINGS

FIG. 3 is perspective view of a board comprising a multiplexed array of plural thermal sensors of the type shown in FIGS. 1 and 2, and illustrating the board connected to a schematic representation of an associated control system.

FIG. 7 is an alternative embodiment of the illustrated invention including an analytical reagent chamber fluidly connected the thermal sensor for introduction of a reagent into the sensor during analysis.

DETAILED DESCRIPTION OF ILLUSTRATED EMBODIMENTS

The illustrated invention provides an apparatus for rapidly capturing environmental compounds such as inorganic and organic molecules, and for qualitative and quantitative analysis of the captured compounds. While the inventive apparatus may be used in numerous situations, it is especially useful for on-site field analysis where more traditional sample collection and analytical instruments are difficult or impossible to use.

Figure 1:
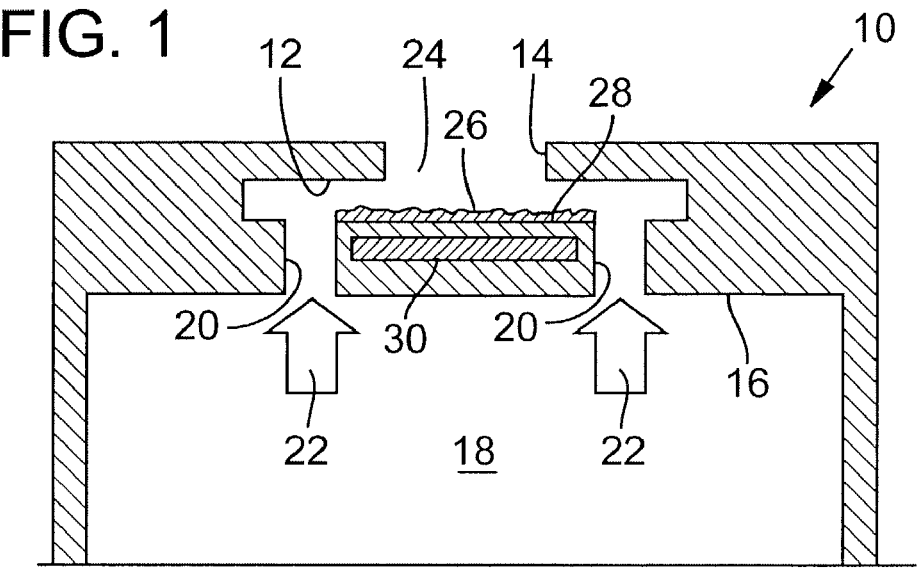
FIG. 1 is an enlarged cross sectional, schematic view of a single thermal sensor formed in accordance with the illustrated embodiment of the invention.

FIG. 1 is a schematic reproduction in a graphic form of a single thermal sensor 10 configured for the performance of environmental sensing and analysis in accordance with one aspect of the illustrated invention. As detailed below, it will be appreciated that the single sensor 10 illustrated in FIG. 1 typically is combined with many other similar sensors in a multiplexed array or sensor "bank" that facilitates chemical analysis on a single integrated circuit chip. Such an array of plural sensors 10 is shown in FIG. 7 and is described below. A single sensor is nonetheless described at this point with reference to FIGS. 1 and 2 to provide detailed information about the structure and operation of the sensors.

Sensor 10 is depicted in cross section in FIG. 1. For modeling purposes, sensor 10 is defined by a substrate member 16 that has a solid orifice structure 12 constructed as a generally planar upper surface having a circular orifice 14 defined in it. The orifice structure 12 defines an opening in substrate member 16 into a reaction chamber 24, and substrate member 16 further defines a sample inlet chamber 18 opposite of and underlying reaction chamber 24. As detailed below with reference to FIG. 2, substrate member 16 may be a multi-layer structure, or may be monolithic as shown in FIG. 1. Two inlets 20 are defined in the substrate member 16 to allow a sample fluid to flow (as depicted by arrows 22) from sample inlet chamber 18 into reaction chamber 24.

The reaction chamber 24 defines a small reservoir for holding a sample fluid to facilitate reaction of agents contained in the fluid with a thin layer of a sorbant material 26 that is deposited on and adhered to a reaction surface 28 that lies within reaction chamber 24.

Sorbant material 26 is selected according to the desired target compounds that are of interest, and which are referred to herein as "agents." Generally speaking, sorbant material 26 may be selected from the numerous available sorbants designed to attract organic and inorganic compounds. For example, sorbant material 26 may be selected from the classes of chemical sorbants commonly used in chromatographic columns. There are a wide variety of such sorbants available on the commercial market, and the specific type of sorbant selected depends upon numerous factors, including for instance the type of agents that are of interest, the size of the molecule, polarity, solubility, the environmental operating conditions, etc. Those of ordinary skill in the art are well suited to select an appropriate sorbant material 26. Some of the many suitable sorbants that may be used with sensor 10 and which are readily available include, for example, chromatographic matrices such as cross-linked cellulose or agarose, adsorbents used in liquid chromatography, and sorbants of the types often used in thin layer chromatography. Preferably, the sorbant material 26 is capable of being sputter coated onto reaction surface 28 during fabrication of the sensor 10.

Returning to FIG. 1, a heat transducer 30 is formed in substrate member 16 such that the transducer underlies reaction surface 28. Heat transducer 30 is capable of being energized to heat the reaction surface. For illustrative purposes the heat transducer 30 is considered to be a planar member such as a thin-film resistor that, upon actuation with a pulse of electrical current, provides an energy density sufficient to heat reaction surface 28 and sorbant material 26 sufficiently to volatilize molecules of interest that are captured on sorbant material 26. The energy density required to volatilize compounds of interest varies depending upon numerous factors, such as the type of sorbant material 26 used, the temperature necessary to volatilize agents bound on the sorbant material, and the size of the reaction surface. The area dimensions of reaction surface 28 are determined by the analytical thresholds of the analytical instruments that are being used with the invention, as described below.

Figure 2:
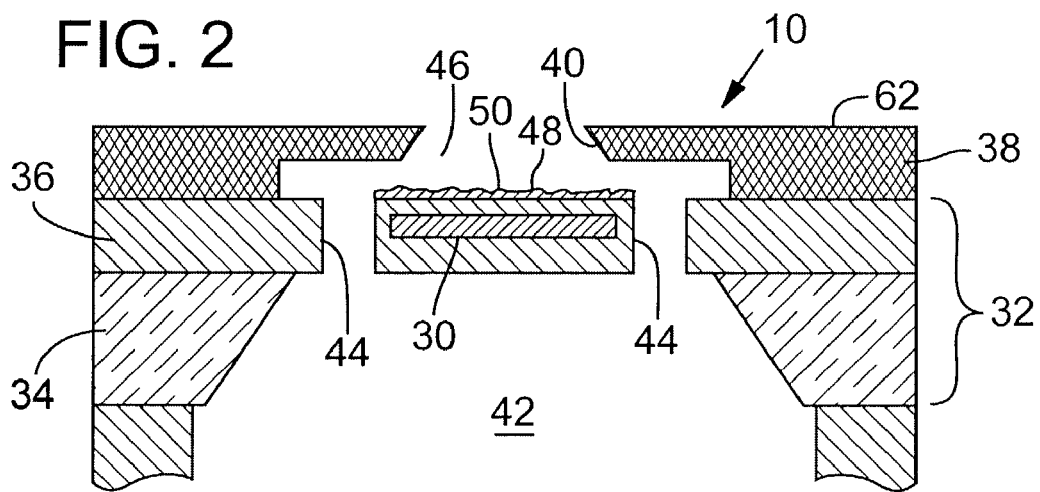
FIG. 2 is an enlarged cross sectional, schematic view of a single thermal sensor formed in accordance with the illustrated embodiment of the invention, similar to the thermal sensor illustrated in FIG. 1 and showing different structural features.

Having described generally a single thermal sensor 10 according to the illustrated embodiment, one approach to fabricating a thermal sensor 10 in accordance with the illustrated invention follows with reference to FIG. 2. Thermal sensor 10 shown in FIG. 2 shows a greatly enlarged cross section of the sensor 10 formed in accordance with the illustrated invention and somewhat more detailed than the sensor 10 illustrated in FIG. 1. As with the single sensor 10 shown in FIG. 1, for illustrative purposes, only one sensor is shown in FIG. 2. But as noted above, and as will become clear, the fabrication process allows the production of multiple sensors in a multiplexed sensor array. The number of sensors produced in any multiplexed array depends number of reaction chambers that are required or desired in a given application.

The exemplary sensor 10 shown in FIG. 2 includes a rigid substrate 32 that can be defined by a silicon base layer 34, which is preferably a conventional silicon wafer upon which has been grown an insulation layer, such as silicon dioxide. The substrate 32 includes a control layer 36 that overlies the silicon base layer 34. Individual heat transducers 30 are defined as portions of the control layer 36 and are fabricated of an appropriate resistive material, such as tantalum aluminum. Each heat transducer 30 is individually connected by a conductive layer to traces on a flex circuit 60 (see FIG. 3) that, as described more fully below, connects with a control system 68 for operating the sensors 10. There typically is a heat transducer 30 associated with each sensor 10.

The substrate layer 32 may incorporate CMOS circuit components for permitting the use of multiplexed control signals for energizing individual heat transducers 30. In addition to the simplified connection with the heat transducers 30, the control logic afforded by the CMOS circuitry enables, for example, precise heating control for individual sensors 10 or groups of sensors, including gradually increased heating to volatilize different compounds at different times and temperatures.

An orifice layer 38 is fixed to the control layer 36 and defines the orifice 40, which is preferably circular. As described above with reference to FIG. 1, a sample inlet chamber 42 communicates via inlets 44 with a reaction chamber 46 adjacent orifice 40. Reaction surface 48 is located in reaction chamber 46 and is bounded by control layer 36 and orifice layer 38. The reaction surface is heated with heat transducer 30, and is coated with a thin layer of sorbant material 50 as detailed above. Thus, reaction chamber 46 is a bounded chamber having inlets 44 and an orifice 40. As described in detail below, a sample fluid, which may be gaseous or liquid, is introduced into reaction chamber 46 through inlets 44. The fluid is allowed to remain in the reaction chamber for a period of time sufficient for agents of interest contained in the fluid to be bound to sorbant material 50.

The thermal sensors 10 shown in FIGS. 1 and 2 are configured for use in the rapid qualitative and quantitative identification of environmental agents such as organic and inorganic molecules. This broad range of compounds is referred to herein generically as "agents." As used herein, therefore, the term "agent" refers generally to compounds such as inorganic or organic molecules present in a sample and which may be bound to sorbant material 26, 50 and volatilized from the sorbant material when heated with the heat transducer.

Turning now to FIG. 3, a multiplexed array 60 comprising numerous individual thermal sensors 10 are provided on a single board 62. It will be appreciated that board 62 is fabricated according to standard circuit board processing methods, and as noted above, includes circuitry such as CMOS components and the like. As such, board 62 is sometimes referred to herein as "circuit board 62," as it thus defines a multiplexed array of thermal sensors 10 on a single integrated circuit "chip." Each thermal sensor 10 is of the type described above with respect to FIGS. 1 and 2, and the sorbant material 26 deposited onto the reaction surfaces may be either the same in each sensor 10, or may be different as in the case where each sensor is designed to attract and bind a different agent or class of agents.

Each sensor 10 in array 60 includes an individual conductive layer as described above that connects each heat transducer 30 individually to a controller 64 via a suitable interconnect such as flex circuit 66. Controller 64 is a component of a control system 68, which includes a power supply 70 and an operator control interface, shown generically in FIG. 3 as a switch 72, although it is to be appreciated that the operator control interface will include other control apparatus such as display monitors and the like well known to those of ordinary skill in the art. The control system 68 typically is a remote microprocessor that may be connected to circuit board 62 at desired locations and at desired times to facilitate operation of the array 60. It will be appreciated that the control system may be configured in any number of ways, including as an integral component of the board 62 in an integrated unit, and that control system 68 includes necessary operating software.

The multiplexed array 60 illustrates a single board array having ten columns of individual thermal sensors 10. The columns in FIG. 3 are labeled with reference numbers 80, 82, 84, 86, 88, 90, 92, 94, 96, and 98. Each of these columns includes ten sensors 10, thus defining ten rows of sensors, labeled 102, 104, 106 and so on through 116. Array 60 thus includes 100 individual sensors 10, each of which is of the type illustrated in FIGS. 1 and 2. The sorbant material deposited on the reaction surface in any one of the individual sensors 10 may be of a different type from the sorbant material used in any other individual sensor 10. Thus, and by way of example, each of the ten sensors 10 in column 80 may have a reaction surface 28 coated with a first sorbant material 26 designed to attract a first type of agent. The ten sensors 10 in adjacent column 82 may include a second, different sorbant material 26 designed to attract a different type of agent more strongly than the sorbant material 26 in sensors 10 in column 80, and so forth. It will be appreciated that any number of combinations of sorbant materials are possible, thereby allowing for differential attraction of various agents in different sensors 10 provided on a single board such as board 62. Because each individual sensor 10 is separately connected to control system 68, each sensor may be individually activated and agents bound to the sorbant material 26 in each sensor may be individually analyzed.

Multiplexed array 60 is designed especially for use in the field to analyze environmental agents present in a location. Because the circuit board 62 is primarily a silicon material it may be used in harsh environments and environments that may be toxic to humans. As detailed below, the array 60 may be placed in a location to allow collection of a sample without the control system 68. The "exposed" array may then be removed from the environment and connected to the control system for analysis at a different location. Moreover, because the board 62 and individual sensors 10 may be miniaturized, the board may be installed and used in numerous locations that would not be suitable for installation of larger, more traditional sensing apparatus.

Figure 4:
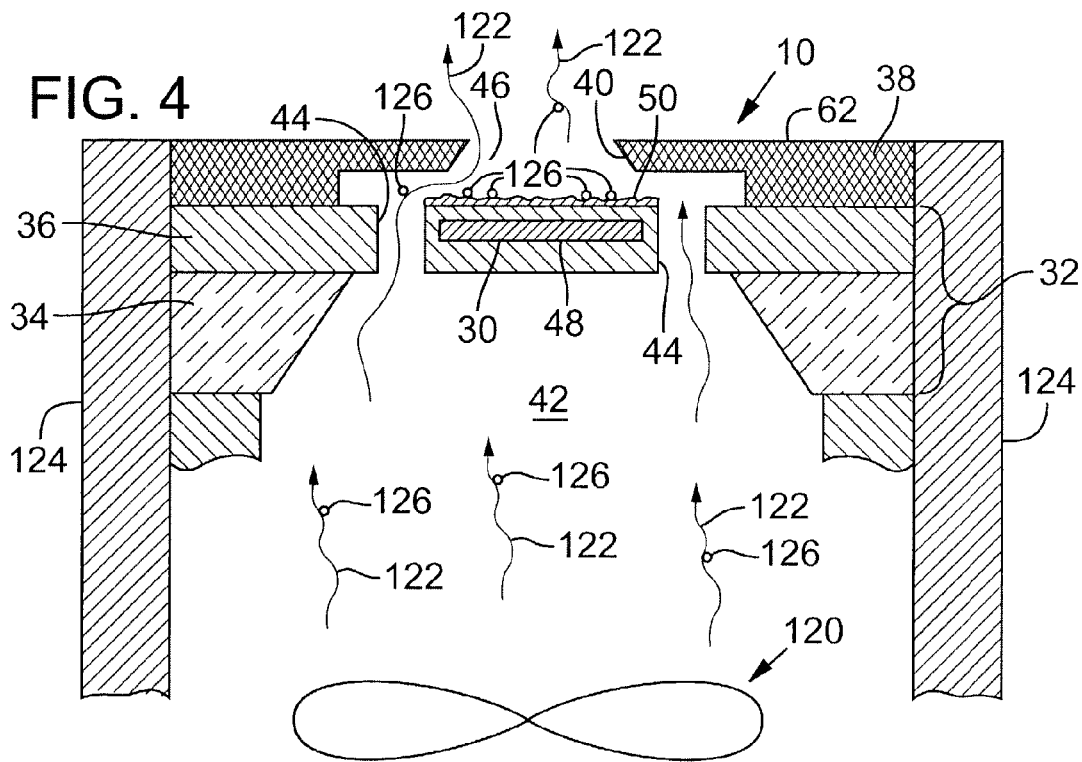
FIG. 4 is a schematic view of a thermal sensor as illustrated in FIG. 2 and adapted for exposure to a sample fluid.

The multiplexed array 60 may be used to analyze liquid or gaseous sample fluids. In either case, the array is used with means for exposing each sensor to the sample fluid. Referring to FIG. 4, an individual sensor 10 is shown schematically with a fan 120 positioned below sample inlet chamber 42 so that a sample fluid—in this case a gas represented by arrows 122—is forced through sample inlet chamber 42, through inlets 44 and through reaction chamber 46. Sample fluid 122 includes agents of interest, shown schematically as agent 126. It will be appreciated that fan 120 represents only one means by which a sample fluid may be introduced into reaction chamber 46, and that where a fan 120 is used, the circuit board 62 will include a housing to hold the circuit board in position relative to the fan, such as housing 124, which is shown schematically in FIG. 4. It will further be appreciated that where the sample fluid is liquid rather than gaseous, different means may be used to induce a flow of the sample fluid into reaction chamber 46.

Regardless of the means by which a sample fluid such as sample fluid 122 is introduced into reaction chamber 46, the sample fluid is allowed to remain in reaction chamber 46 for a sufficient amount of time to allow agents 126 in the sample fluid to be attracted to sorbant material 50. As noted, different sensors 10 in array 60 may be coated with different sorbant materials that more strongly attract some molecular species over others. Once the sensor(s) have been exposed to a sample fluid for a sufficient period of time to allow the agents 126 to bind to the sorbant material 50, the array 60 is set up for analysis of the agents. In FIG. 4, agents 126 are shown schematically as being bound to sorbant material 50. It will be appreciated that in most instances a sample fluid such as sample fluid 122 will be a heterogeneous mixture that includes several chemical species, and that several different species will be attracted to sorbant material 50. The drawing figures are highly schematic to represent only one such agent. Moreover, different agents will be "bound" to the sorbant material in different manners. Some agents will be chemically bonded to the sorbant; others will be physically bound in a matrix structure, and so forth. The present discussion contemplates all types of such attraction and refers to them generally as being "bound" to the sorbant.

Figure 5:
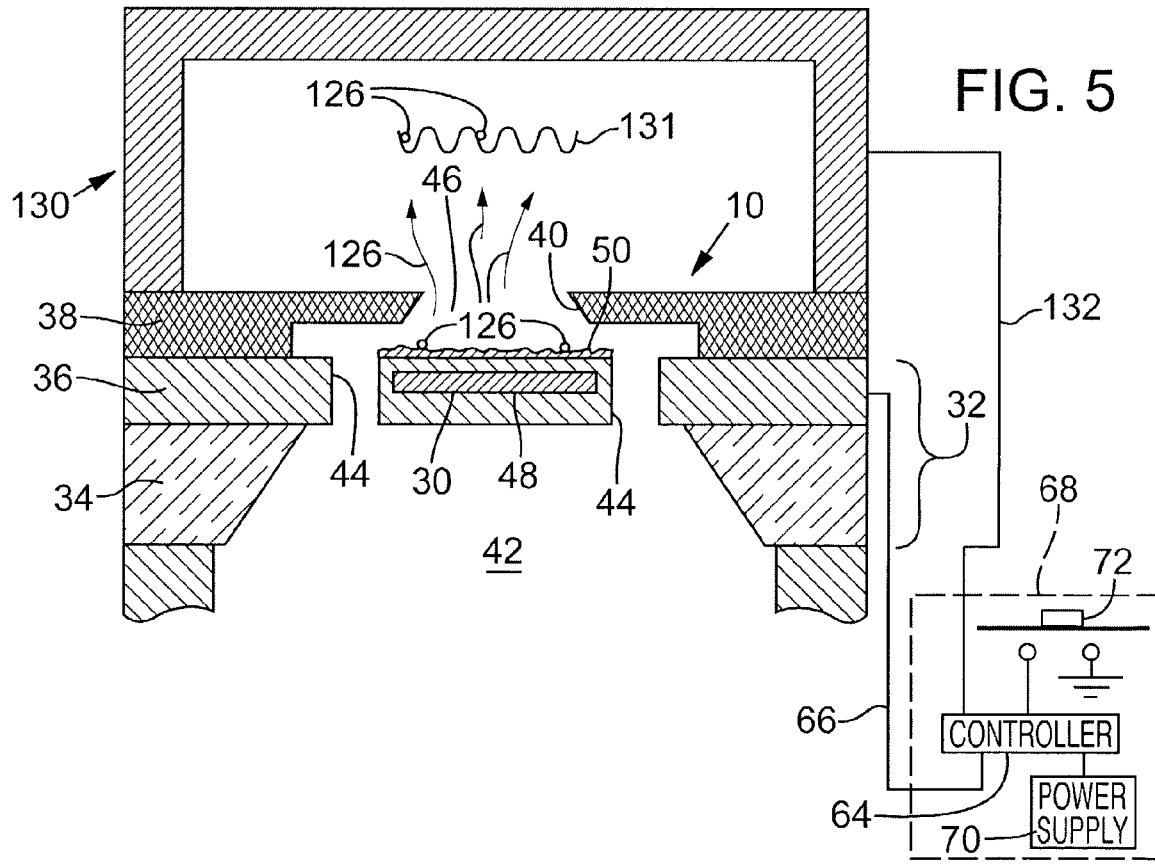
FIG. 5 is a schematic view of the thermal sensor illustrated in FIG. 4 and adapted for analytical analysis of chemical agents bound to the sorbant material in the sensor.

Analysis of agents such as agents 126 bound to sorbant 50 requires an analytical instrument and may be performed either on-site at the location where the sample fluid was taken, or remotely, for instance at a lab. In either case, and as detailed below, several types of analytical analysis may be performed. Regardless of the type of analytical instrument used to quantify and qualify the agents 126, the instrument is adapted so that one or more of the orifices 40 are fluidly ported into the instrument. This fluid connection is schematically illustrated in FIG. 5, where an analytical instrument 130 is shown schematically and in proximity to sensor 10 such that orifice 40 ports to and exhausts into the analytical instrument. Analyzer 130 may be any kind of analytical instrument adapted for use with an array 60, including for example a gas chromatograph, mass spectrophotometer, atomic absorption spectrophotometer, etc. Analyzer 130 includes a detector head 131, shown generically, where agents 126 volatilized off of sorbant material 50 are detected. Detector head 131 is connected via circuitry 132 to control system 68. As discussed above, heat transducer 30 is likewise connected to control system 68. It will be appreciated that analyzer 130 may be utilized with a separate control system. It also will be appreciated that the surface of sensor 10 around an orifice (such as orifice 14 in FIG. 1) may be micro machined to facilitate a fluid-tight connection between the orifice and the inlet port on the analyzer.

Analysis of agents, e.g., particles 126 bound on the sorbant material 50 is begun by first activating the control system 168 so that a flow of fluid sample is introduced into the reaction chamber. The flow of fluid may be induced by numerous means, including mechanical flow induction such as with a fan, passively, or by using pressure differentials. Depending upon the structure of the thermal sensor used, the method of inducing a flow of fluid sample may, for example, comprise turning on fan 120. Sample fluid is allowed to remain in the reaction chamber 46 for a predetermined minimal amount of time sufficient to allow agents 126 contained in the sample fluid 122 to bind to the sorbant material 50. The heat transducer 30 is then energized by the control system 168 to cause the transducer to heat up. As the transducer heats, the reaction surface 48 is heated, as is sorbant material 50. Heating the sorbant material volatilizes particles 126, which are ejected through orifice 40 into analyzer 130 where they are characterized. Analyzer 130 may be configured for either qualitative or quantitative analysis, or both, of the agent or agents volatilized from the sorbant material. Analyzer 130 may be adapted to analyze agents volatilized from a selected sensor 10 energized (or "fired") one at a time, or from multiple sensors fired simultaneously. Moreover, each sensor may be energized in a predetermined and controllable manner to selectively volatilize specific agents of interest. For example, the heat transducers may be heated gradually so that different molecular species volatilize from sorbant material at different times. The ability to precisely control the temperature of the reaction surface and the rate at which it is heated allows for precise control of the release of agents from the sorbant and into analyzer 130. It will be appreciated that control system 68 includes processors having appropriate processing capabilities, hardware and software, to analyze data received from analyzer 130 and to provide meaningful analytical data. As an example, control system 68 is configured for analyzing data with predetermined algorithmic calculations and generating an output signal to an appropriate display (not shown), which may be any appropriate display such as a visually detectable unit such as a CRT or LCD screen, or as simple as an audible message generator such as a transducer.

After analysis of any one or more of the agents 126 bound to sorbant material 50 is complete, the heat transducers may continue to be heated so that all chemical species bound to the sorbant material is desorbed, essentially cleaning the sensors for reuse.

Figure 6:
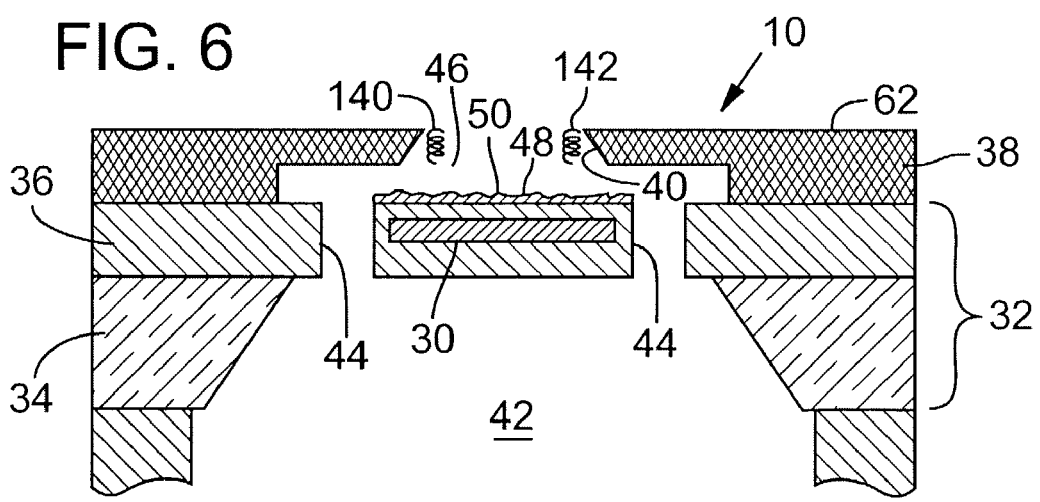
FIG. 6 is an enlarged cross sectional, schematic view of a single thermal sensor formed in accordance with the illustrated embodiment of the invention, similar to the thermal sensor illustrated in FIG. 2 and showing electrodes defining an analyzer integrated into the thermal sensor.

As an alternate to more traditional analyzers 130 such as those described above, each thermal sensor 10 may be adapted for on-chip analysis of agents volatilized from the sensor. Specifically, with reference to FIG. 6, a pair of closely spaced electrodes, shown schematically as electrodes 140, 142 may be placed in the fluid path from reaction chamber 46, for example at orifice 40, and such that agents desorbed from sorbant material 50 in the manner just described flow past the electrodes. The electrodes 140, 142 are connected to control system 68 and are configured to measure the electrical conductance of the volatilized agents, either with or without ionization. The data thus obtained is processed in control system 68 according to predetermined algorithms to characterize the agents. With appropriate circuitry, one or both of the electrodes may be provided by one or more opposed edges of the orifice 40. By slowly increasing the temperature of the reaction surface, different agents bound to the sorbant material are selectively desorbed at different temperatures, allowing for separate detection and analysis of separate agents. Alternately, data output from electrodes 140, 142 may be conditioned and processed by circuitry and control components that are an integral part of the circuit board 62.

Sometimes it is desirable to have a chemical reaction occur between the agent and a reagent prior to analysis. For example, some chemical compounds are more readily detected and analyzed as moieties formed by reaction of the compound with a reagent. Also, some chemical species bound to the sorbant may be released more readily therefrom in the presence of a solvent. The thermal sensor according to the illustrated invention is adaptable in several different ways to accommodate such reactions. Referring to FIG. 7, one possible apparatus for introducing a reagent into reaction chamber 46 of a thermal sensor 150 is illustrated. Thermal sensor 150 is identical to the thermal sensors 10 described above except that the reaction chamber 46 includes a reagent inlet 152 that defines a fluid passageway 154 from a reagent chamber 156. Reagent chamber 156 is preferably formed in the same circuit board material as thermal sensor 150 and is structurally similar to the sensor. Thus, reagent chamber 156 includes a reaction surface 158, and a heat transducer 160 located in close proximity to the reaction surface so that it heats the reaction surface when the transducer is fired.

A supply of a selected reagent 168 is deposited onto reaction surface 158, with appropriate binders as needed. Reagent chamber 156 is a bounded space that includes an orifice 162 that leads to fluid passageway 154. An inlet passageway 164, shown in dashed lines because it is optional, may be provided from a reagent reservoir 166 when there is a need for replenishing the supply of reagent 168, which travels into reagent chamber 156 in the direction indicated by arrow 170.

The thermal sensor 150 shown in FIG. 7 is operated in the same manner described above to expose sorbant material 50 to a sample and to thereby bond agents of interest to the sorbant material. Once the sorbant material has been exposed to the fluid sample for a sufficient period of time, the reagent may be introduced into reaction chamber 46. This may be done in any one of several ways. As a first alternative, the heat transducer 160 in reaction chamber 156 may be fired prior to energizing heat transducer 30 in reaction chamber 46. As reaction surface 158 is heated, reagent 168 is volatilized from the reaction surface and flows through passageway 154 as indicated with arrows A, and as shown schematically with reagent 168, shown in FIG. 7 as discrete particles. The reagent 168 flows into reaction chamber 46 through inlet 152 and settles onto sorbant material 50 where the reagent reacts with selected agent(s) bonded to the sorbant material. The heat transducer 30 is then energized and the moiety formed by reaction of reagent 168 with the agent of interest on sorbant material 50 volatilizes from reaction surface 48, flows through orifice 40 for analysis by an analytical instrument as described above.

Alternately, heat transducer 160 may be fired shortly before or simultaneously with heat transducer 30. In that case the reagent 168 and the agent that has been volatilized off of reaction surface 48 then mix in the space above the reaction surface in reaction chamber 46, react in the gaseous state, and flow through orifice 40 into the analytical instrument.

The illustrated invention is capable of being used in harsh environments for rapid detection and analysis of a wide variety of organic and inorganic compounds. As such, it is capable of providing ongoing monitoring feedback information relating to effluent output in waste-stacks and wastestreams and the like. The invention may include, where appropriate, an associated analytical instrument of any of the kinds described above.

Those having ordinary skill in the art will understand that the invention illustrated in the drawings and described herein may be modified in various respects without materially altering the invention. For example, the number of inlet pathways into the reaction chamber may be increased or decreased according to need, and their positions relative to the reaction surface may likewise be changed so long as a sample fluid is conducted through the inlets to the reaction chamber and the sorbant material. Further, in some instances the inlet into the reaction chamber may be defined by the orifice. That is, the reaction chamber may be bounded completely and open only at the orifice. In this case sample fluid enters the reaction chamber through the orifice, is allowed to remain in the reaction chamber for a period of time to allow bonding to the sorbant material before heating the heat transducer to volatilize the agents bound thereto.

Having here described illustrated embodiments of the invention, it is anticipated that other modifications may be made thereto within the scope of the invention by those of ordinary skill in the art. It will thus be appreciated and understood that the spirit and scope of the invention is not limited to those embodiments, but extend to the various modifications and equivalents as defined in the appended claims.

The invention claimed is:

1. A chemical preconcentrator, comprising:
a substrate having plural sample chambers, each at least partially bounded by the substrate and each associated with a separate reaction chamber that is at least partially bounded by the substrate, a passageway extending through the substrate from each sample chamber into the associated reaction chamber to define an inlet for conducting fluid from the sample chamber into the reaction chamber, a reaction surface within each reaction chamber and an orifice in the substrate adjacent the reaction surface defining an outlet from the reaction chamber;
a sorbant deposited on the reaction surface;
a heat transducer in the substrate between the sample chamber and the reaction chamber in proximity to the reaction surface and configured for heating the reaction surface; and
a control system configured for energizing separately selected heat transducers.

2. The chemical preconcentrator according to claim 1 including different sorbants in different reaction chambers, and wherein each sorbant is selected for an ability to bind a different agent.

3. The chemical preconcentrator according to claim 1 including an analytical instrument fluidly connected to the orifice.

4. The chemical preconcentrator according to claim 1 including a reagent inlet into the reaction chamber for conducting a reagent into the reaction chamber.

5. The chemical preconcentrator according to claim 4 further including a second substrate defining a reagent reservoir fluidly connected to the reagent inlet.

6. The chemical preconcentrator according to claim 5 wherein the reagent reservoir includes a reaction surface, a heat transducer in proximity to the reaction surface and configured for heating the reaction surface, and a reagent deposited on the reaction surface.

7. The chemical preconcentrator according to claim 1 including means for creating a flow of a sample fluid through the Inlet into the reaction chamber.

8. The chemical preconcentrator according to claim 7 wherein the means for creating a flow of a sample fluid comprises a fan.

9. A method of analyzing agents in a sample, comprising the steps of:
(a) providing a chemical preconcentrator comprising a substrate having a sample chamber and a reaction chamber, each at least partly bounded by the substrate, a passageway from the sample chamber through the substrate into the reaction chamber to define an inlet to the reaction chamber from the sample chamber, a reaction surface In the reaction chamber having a sorbant deposited thereon, and an orifice adjacent the reaction surface defining an outlet from the reaction chamber;
(b) introducing a sample liquid from the sample chamber into the reaction chamber through the inlet and allowing the sample liquid to remain in the reaction chamber for a period of time sufficient for agents contained in the sample to be bound to the sorbant and thereby preconcentrate the agents;
(C) energizing a heat transducer to heat the reaction surface and to thereby volatilize the agents such that the volatilized agents exit the reaction chamber through the orifice;
(d) capturing the volatilized agents in an analyzer to characterize the agents.

10. The method according to claim 9 wherein the energizing step causes the reaction surface to be heated at a controlled rate.

11. The method according to claim 9 including the step prior to step (c) of introducing a reagent into the reaction chamber and allowing the reagent to react with the agents.

12. The method according to claim 9 wherein the analyzer is a component of the chemical preconcentrator.

13. The method according to claim 9 including the step of continuing heating of the reaction surface to desorb all agents bound to the sorbant.

14. Apparatus for detecting agents in a fluid sample, comprising:
preconcentrator means for binding agents in the sample to a sorbant-coated reaction surface in a reaction chamber in said preconcentrator means, said preconcentrator means having plural sample chambers and plural reaction chambers, each sample chamber associated with a reaction chamber and each reaction chamber having a sorbant-coated reaction surface, and an inlet from each sample chamber into the associated reaction chamber, and an outlet from each reaction chamber defined by an orifice in said preconcentrator means;
heating means for heating selected reaction surfaces to volatilize agents bound to the sorbant in selected chambers, said heating means including a heating element located in the preconcentrator means between the sample chamber and the selected reaction chamber;
controller means for energizing the heating means at a predetermined time and at a controlled rate;
analyzer means for receiving agents volatilized from the reaction chamber and characterizing the agents.

15. The apparatus according to claim 14 wherein the preconcentrator means further comprises a unitary integrated circuit substrate defining for each reaction chamber an inlet is configured for conducting the associated sample into the reaction chamber, a reaction surface and an orifice adjacent the reaction surface defining an outlet configured for conduction sample from the reaction chamber, a sorbant deposited on the reaction surface, and a heat transducer in proximity to the reaction surface and configured for heating the reaction surface.

16. Apparatus for preconcentrating compounds in a sample, comprising:
a unitary integrated circuit substrate member having plural reaction chambers and a sample chamber associated with each reaction chamber, each reaction chamber having a heat transducer in proximity to an interior surface thereof defining a reaction surface and such that the heat transducer is capable of heating the reaction surface, said heat transducer positioned between the sample chamber and the reaction chamber, and the substrate member further defining a passageway from the sample chamber to the reaction chamber through which compounds are conducted into the reaction chamber from the sample chamber and an orifice through which compounds are conducted Out of the reaction chamber;
a sorbant deposited on the reaction surface;
a control system connected to each heat transducer and configured to energize selected heat transducers to selectively heat individual reaction surfaces.

17. The apparatus according to claim 16 wherein individual reaction chambers may be heated at a controlled rate.

18. The apparatus according to claim 17 including different sorbants in different reaction chambers.

19. The apparatus according to claim 16 including a reagent inlet into the reaction chamber for conducting a reagent into the reaction chamber.

20. The apparatus according to claim 16 including means for creating a flow of the sample through the inlet into the reaction chamber.

21. A method of detecting the presence of a chemical in a sample, comprising the steps of:
   (a) inducing a flow of a sample from a sample chamber through a passageway and into a reaction chamber of a chemical preconcentrator, the preconcentrator comprising a unitary substrate member that at least partially bounds plural sample chambers and plural reaction chambers, each sample chamber associated with a reaction chamber, and the substrate member having a heat transducer between each sample chamber and the associated reaction chamber in proximity to an interior surface of the reaction chamber defining a reaction surface within each reaction chamber, and a sorbant deposited on each reaction surface;
   (b) allowing the sample to remain in the reaction chamber for a period of time sufficient to bind agent in the sample to the sorbant:
   (c) heating the reaction surface in a selected reaction chamber to volatilize the agent;
   (d) capturing and detecting the agent volatilized from the selected reaction chamber in an analyzer.

22. The method of claim 21 wherein the detecting step includes the step of characterizing the agent.

23. The method of claim 21 Including the step of continued heating of the reaction surface to volatilize all agent bound to the sorbant.

* * * * *

UNITED STATES PATENT AND TRADEMARK OFFICE
CERTIFICATE OF CORRECTION

PATENT NO. : 7,172,730 B2
APPLICATION NO. : 10/315461
DATED : February 6, 2007
INVENTOR(S) : Steven E. Carpenter It is certified that error appears in the above-identified patent and that said Letters Patent is hereby corrected as shown below:

In column 9, line 42, in Claim 7, delete "Inlet" and insert -- inlet --, therefor.

In column 9, line 54, in Claim 9, delete "In" and insert -- in --, therefor.

In column 9, line 64, in Claim 9, delete "(C)" and insert -- (c) --, therefor.

In column 10, line 59, in Claim 16, delete "Out" and insert -- out --, therefor.

In column 11, line 13, in Claim 21, delete "preconcetrator" and insert -- preconcentrator --, therefor.

In column 12, line 7, in Claim 21, delete "sorbant:" and insert -- sorbant; --, therefor.

In column 12, line 14, in Claim 23, delete "Including" and insert -- including --, therefor.

In column 12, line 15, in Claim 23, delete "agent" and insert -- agents --, therefor.

Signed and Sealed this

Thirty-first Day of March, 2009

JOHN DOLL
*Acting Director of the United States Patent and Trademark Office*